US010500584B2

(12) United States Patent
Kisner et al.

(10) Patent No.: US 10,500,584 B2
(45) Date of Patent: *Dec. 10, 2019

(54) CHEMICAL SEQUENCING AND CONTROL TO EXPAND AND ENHANCE DETECTION CAPABILITIES UTILIZING A COLORIMETRIC TEST

(71) Applicant: DetectaChem, Inc., Stafford, TX (US)

(72) Inventors: Mark A. Kisner, Sugar Land, TX (US); Travis R. Kisner, Sugar Land, TX (US)

(73) Assignee: DETECTACHEM, INC., Stafford, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,647

(22) Filed: Jun. 30, 2017

(65) Prior Publication Data

US 2017/0297014 A1     Oct. 19, 2017

Related U.S. Application Data

(63) Continuation of application No. 14/646,105, filed as application No. PCT/US2013/032603 on Mar. 15, 2013.

(Continued)

(51) Int. Cl.
*G01N 21/75* (2006.01)
*G01N 31/22* (2006.01)
(Continued)

(52) U.S. Cl.
CPC ............ *B01L 3/5023* (2013.01); *G01N 21/25* (2013.01); *G01N 21/75* (2013.01); *G01N 21/78* (2013.01);
(Continued)

(58) Field of Classification Search
CPC ........ G01N 21/75; G01N 31/22; G01N 21/25; G01N 2021/754; B01L 3/00
(Continued)

(56) References Cited

U.S. PATENT DOCUMENTS 3,697,227 A * 10/1972 Goldstein et al. ...... B01L 3/502
422/409
3,713,779 A * 1/1973 Sirago ..................... B01L 3/502
206/219

(Continued)

FOREIGN PATENT DOCUMENTS

WO    WO 2012/119128     * 9/2012

*Primary Examiner* — Arlen Soderquist
(74) *Attorney, Agent, or Firm* — Winstead PC

(57) ABSTRACT

Embodiments of the present disclosure pertain to a colorimetric system for detecting a substance, the colorimetric system that includes a first chemical container adapted for releasing a first chemical; a second chemical container adapted for releasing a second chemical; a flow modulation sheet adjacent each chemical container; and an encapsulation covering the flow modulation sheet and each chemical container, where the encapsulation comprises a window defining a target area of the filter paper such that the target area is adapted for applying the substance; where the flow modulation sheet comprises a design adapted for automatically controlling a first flow of the first chemical and a second flow of the second chemical to the target area after simultaneously releasing the first and second chemicals; and where the design comprises a first void disposed in the flow modulation sheet.

15 Claims, 3 Drawing Sheets

Related U.S. Application Data

(60) Provisional application No. 61/728,519, filed on Nov. 20, 2012.

(51) Int. Cl.
  *G01N 21/25* (2006.01)
  *B01L 3/00* (2006.01)
  *G01N 21/78* (2006.01)
  *G01N 21/77* (2006.01)

(52) U.S. Cl.
  CPC ...... *G01N 31/22* (2013.01); *B01L 2200/0636* (2013.01); *B01L 2300/0867* (2013.01); *B01L 2300/0887* (2013.01); *B01L 2400/086* (2013.01); *G01N 2021/754* (2013.01); *G01N 2021/7759* (2013.01)

(58) Field of Classification Search
  USPC .............. 422/401–402, 412–413, 417; 436/164–165
  See application file for complete search history.

(56) References Cited

U.S. PATENT DOCUMENTS

| | | | |
|---|---|---|---|
| 4,473,457 A * | 9/1984 | Columbus | G01N 27/307 204/409 |
| 4,673,657 A * | 6/1987 | Christian | B01J 19/0093 422/301 |
| 4,855,240 A * | 8/1989 | Rosenstein | G01N 33/5302 422/401 |
| 4,857,453 A * | 8/1989 | Ullman | G01N 33/54366 422/430 |
| 4,918,025 A * | 4/1990 | Grenner | B01L 3/5027 422/565 |
| 4,943,522 A * | 7/1990 | Eisinger | G01N 33/54386 422/537 |
| 4,960,691 A * | 10/1990 | Gordon | B01L 3/5023 422/408 |
| 4,965,047 A * | 10/1990 | Hammond | G01N 33/528 422/413 |
| 5,006,474 A * | 4/1991 | Horstman | G01N 33/54366 422/537 |
| 5,110,552 A * | 5/1992 | Guigan | B01L 3/505 356/246 |
| 5,135,872 A * | 8/1992 | Pouletty | B01L 3/502 422/552 |
| 5,154,888 A * | 10/1992 | Zander | B01L 3/502 206/219 |
| 5,198,193 A * | 3/1993 | Bunce | B01L 3/502 422/501 |
| 5,225,163 A * | 7/1993 | Andrews | G01N 33/5302 422/413 |
| 5,275,785 A * | 1/1994 | May | G01N 33/54386 422/408 |
| 5,290,518 A * | 3/1994 | Johnson | B01L 3/502 422/413 |
| 5,422,271 A * | 6/1995 | Chen | B01L 3/502 206/223 |
| 5,458,852 A * | 10/1995 | Buechler | B01J 19/0093 422/417 |
| 5,480,612 A * | 1/1996 | Margalit | G01N 31/22 422/430 |
| 5,516,488 A * | 5/1996 | Bunce | G01N 33/54366 422/412 |
| 5,618,494 A * | 4/1997 | Bunce | B01L 3/502738 422/412 |
| 5,648,047 A * | 7/1997 | Kardish | G01N 21/29 422/411 |
| 5,652,149 A * | 7/1997 | Mileaf | B01L 3/502 422/417 |
| 5,674,653 A * | 10/1997 | Chemelli | B01L 3/505 356/246 |
| 5,679,584 A * | 10/1997 | Mileaf | G01N 21/82 422/411 |
| 5,736,188 A * | 4/1998 | Alcock | B01L 3/5023 106/31.94 |
| 5,798,215 A * | 8/1998 | Cathey | B01F 13/0059 422/504 |
| 5,811,296 A * | 9/1998 | Chemelli | B01L 3/505 206/223 |
| 5,859,375 A * | 1/1999 | Danylewych-May | G01N 1/02 73/863.21 |
| 6,077,711 A * | 6/2000 | Singer | B01L 3/502 422/411 |
| 6,146,589 A * | 11/2000 | Chandler | G01N 33/54366 422/408 |
| 6,228,657 B1 * | 5/2001 | Genovese | G01N 1/2273 422/400 |
| 6,426,230 B1 * | 7/2002 | Feistel | B01L 3/50273 422/430 |
| 6,540,962 B1 * | 4/2003 | Okubo | B01L 3/5027 422/401 |
| 6,582,970 B1 * | 6/2003 | Manita | A47J 27/08 422/400 |
| 6,637,463 B1 * | 10/2003 | Lei | B01F 5/0403 137/803 |
| 6,673,628 B2 * | 1/2004 | Freitag | G01N 33/54366 422/417 |
| 6,689,317 B1 * | 2/2004 | Rees | G01N 33/558 422/417 |
| D502,655 S * | 3/2005 | Huang | D10/81 |
| 7,036,388 B1 * | 5/2006 | Genovese | G01N 1/40 436/181 |
| 7,086,277 B2 * | 8/2006 | Tess | C12Q 1/004 204/403.1 |
| 7,090,803 B1 * | 8/2006 | Gould | B01L 3/5023 422/413 |
| 7,132,078 B2 * | 11/2006 | Rawson | G01N 33/558 422/403 |
| 7,189,522 B2 * | 3/2007 | Esfandiari | G01N 33/538 422/423 |
| 7,267,799 B1 * | 9/2007 | Borich | G01N 21/8483 235/462.11 |
| 7,294,306 B2 * | 11/2007 | Haas | G01N 1/02 422/411 |
| 7,384,599 B2 * | 6/2008 | Brewer | G01N 31/22 422/417 |
| 7,445,753 B1 * | 11/2008 | Kreis | G01N 35/1002 422/430 |
| 7,807,104 B2 * | 10/2010 | Haas | G01N 1/02 422/400 |
| 7,867,445 B1 * | 1/2011 | Haas | G01N 1/02 422/68.1 |
| 7,939,029 B2 * | 5/2011 | Eckels | B01L 3/5029 422/401 |
| 8,012,427 B2 * | 9/2011 | Bommarito | B01L 3/502738 422/400 |
| 8,293,188 B2 * | 10/2012 | Bukhtiyarov | G01N 33/52 422/402 |
| 8,435,462 B2 * | 5/2013 | Bedingham | B01L 3/5025 422/401 |
| 8,551,422 B2 * | 10/2013 | Wan | B01L 3/502746 422/503 |
| 8,603,835 B2 * | 12/2013 | Esfandiari | G01N 33/54386 436/514 |
| 8,669,115 B2 * | 3/2014 | Pagoria | B01L 3/5023 436/164 |
| D714,171 S * | 9/2014 | Hoofnagle | D10/78 |
| 8,845,978 B2 * | 9/2014 | Johnson | G01N 1/02 422/406 |
| 8,980,641 B2 * | 3/2015 | Clift | G01N 21/94 422/69 |
| D727,762 S * | 4/2015 | Kisner | D10/78 |
| 9,207,239 B2 * | 12/2015 | Kasdan | B01L 3/502 |
| 9,250,189 B1 * | 2/2016 | Johnson | G01N 21/78 |
| 9,482,621 B2 * | 11/2016 | Clift | G01N 21/94 |
| 9,724,689 B2 * | 8/2017 | Kisner | B01L 3/5023 |
| 10,203,310 B2 * | 2/2019 | Kisner | G01N 31/22 |

(56) References Cited

U.S. PATENT DOCUMENTS

| | | | | |
|---|---|---|---|---|
| 2002/0142301 | A1* | 10/2002 | Hovig | C12Q 1/6809 435/6.14 |
| 2002/0187076 | A1* | 12/2002 | DiCesare | B01L 3/5029 422/537 |
| 2003/0129767 | A1* | 7/2003 | Bautista | B01L 3/5023 436/178 |
| 2004/0224354 | A1* | 11/2004 | Kambara | B01J 19/0046 435/6.11 |
| 2005/0092063 | A1* | 5/2005 | Tajima | G01N 1/2273 73/23.2 |
| 2005/0101027 | A1* | 5/2005 | Haas | G01N 33/227 436/109 |
| 2005/0181517 | A1* | 8/2005 | Chandler | B01L 3/5023 436/169 |
| 2005/0211559 | A1* | 9/2005 | Kayyem | B01L 3/5027 204/601 |
| 2005/0249641 | A1* | 11/2005 | Blankenstein | B01L 3/502738 422/400 |
| 2006/0092030 | A1* | 5/2006 | Povenmire | G01W 1/00 340/601 |
| 2006/0292040 | A1* | 12/2006 | Wickstead | G01N 21/8483 422/82.05 |
| 2008/0182334 | A1* | 7/2008 | Amisar | G01N 31/22 436/124 |
| 2009/0110605 | A1* | 4/2009 | Kido | B01L 3/5027 422/400 |
| 2009/0325300 | A1* | 12/2009 | Clift | G01N 21/94 436/57 |
| 2010/0014085 | A1* | 1/2010 | Sekimoto | G01N 21/314 356/436 |
| 2010/0093019 | A1* | 4/2010 | Ditcham | B01F 3/12 435/34 |
| 2010/0203578 | A1* | 8/2010 | Geiger | G01N 33/721 435/29 |
| 2010/0229633 | A1* | 9/2010 | Pagoria | B01L 3/5023 73/35.14 |
| 2010/0291588 | A1* | 11/2010 | McDevitt | B01L 3/502715 435/7.2 |
| 2011/0081723 | A1* | 4/2011 | Miller | G01N 21/6428 436/56 |
| 2012/0208299 | A1* | 8/2012 | Esfandiari | G01N 33/54386 436/518 |
| 2012/0270225 | A1* | 10/2012 | Wakeley | B01L 3/502715 435/6.12 |
| 2013/0343645 | A1* | 12/2013 | Dalal | G06K 7/1408 382/162 |
| 2014/0314625 | A1* | 10/2014 | Clift | G01N 21/94 422/82.08 |
| 2014/0322816 | A1* | 10/2014 | Haas | G01N 21/78 436/164 |
| 2016/0041134 | A1* | 2/2016 | Kisner | G01N 31/22 436/81 |

\* cited by examiner

CHEMICAL SEQUENCING AND CONTROL TO EXPAND AND ENHANCE DETECTION CAPABILITIES UTILIZING A COLORIMETRIC TEST

CROSS-REFERENCE TO RELATED APPLICATIONS

This application is a continuation of U.S. patent application Ser. No. 14/646,105, filed on Mar. 15, 2013 and issued as U.S. Pat. No. 9,724,689 on Aug. 8, 2017, which is a national stage application of PCT/US2013/032603 that claims priority to U.S. Provisional Patent Application No. 61/728,519 filed on Nov. 20, 2012. The entirety of each of the aforementioned applications is incorporated herein by reference.

STATEMENT REGARDING FEDERALLY SPONSORED RESEARCH

Not applicable.

BACKGROUND

Colorimetric testing is utilized in many industries to determine the presence or degree of presence, e.g. concentration in solution, of particular substances. For example, chlorine test kits have been used to determine the general concentration of chlorine level in swimming pools. In another example, early pregnancy tests detect the presence of a certain hormone in female during pregnancy. Both of these examples illustrate the use of a colorimetric test to determine the presence or degree of presence of a substance. In these examples, the color change is visible to the human eye and is typically observed directly by a person conducting the test.

United States Patent Application Publication US20090325300 describes a card component for use in conjunction with a spectral detection unit useful for detecting trace materials including biohazards, toxins, radioactive materials, narcotics, and explosives. In particular, US20090325300 discloses, at paragraph [0043], that a sample of an unknown trace material is collected on a card component. Reaction of the unknown trace materials sample collected on the on the pad is initiated with liquid reagents and dissolved compounds contained in at least one flexible walled capsule embedded in the card component, wherein the reaction is initiated after inserting the card in the chemical detection unit causing walls of the capsules to yield to fluid flow, establishing fluid communication between the capsules and the pad. This is accomplished by releasing chemicals and other contents of the first capsule and applying heat to stimulate reaction with the unknown trace material. The fluid communication may be established via specific paths like grooves or similar structural means, or using wicks. Further, chemicals from the capsules may be released in a fashion to react in spatially distinct regions of the pad or the regions may be temporally separated for chemical reactions. The spectral pattern is observed and recorded by the chemical detection unit. With respect to release of chemicals from capsules to react in spatially distinct regions of the reaction pad, US20090325300, at paragraph [0047] discloses that that in an embodiment the reaction pad can be divided into three separate fluid channels each in proximity to a specific capsule. In this way three separate color reactions can be produced spatially in a side-by-side configuration rather than in timed sequence. With respect to release of chemicals from capsules to temporally separated regions of the reaction pad, US20090325300, at paragraph [0049], discloses that in one preferred embodiment the first of two capsules capsule is activated and any sequence of color changes is recorded. The second capsule is then activated and the color recorded.

In some colorimetric tests a prior chemical reaction modifies the characteristics of the substance under test in order to be able to execute a subsequent test that requires molecular modification prior to testing for a particular substance. A well-known example is the application of the Griess reaction as the second stage of a two stage reaction scheme to detection of nitroglycerin. The reaction scheme involves two solutions. In the first stage, the reaction scheme involves adding a preliminary alkaline solution containing a base to nitroglycerin to produce nitrite ions. In the second stage, the reaction scheme involves adding an acidic solution Griess reagent mixture to the nitrite ions to produce a colored product. An exemplary base is sodium hydroxide. An exemplary acid Griess reagent mixture includes sulphanilamide and 2-naphthylamine in a phosphoric acid solution. The Griess reaction involves reaction of sulphanilic acid with the nitrites to produce diazonium ions, coupled with reaction of the dizonium ions react with 2-naphthylamine to produce a colored Griess reaction product, both occurring in the same Griess solution. It is desirable to time adding the preliminary alkaline solution containing a base prior to adding the acidic Griess solution containing the Griess reagent mixture because the reaction conditions of the first stage are alkaline and the reaction conditions of the Griess reaction are acidic, therefore differing in pH. Combining the alkaline and acidic solutions would tend to neutralize the pH, thus negatively affecting the test.

Notwithstanding the above teachings, there remains a need for colorimetric test systems and methods that provide for accurate timing control and sequencing of different chemicals. More particularly, there remains a need for colorimetric systems and methods for controlling the arrival of chemicals to a reaction pad in a colorimetric card that do not require temporally separate release of the chemicals.

SUMMARY

In some embodiments, the present invention provides a colorimetric system and method for controlling the arrivals of chemicals to a target area after simultaneous release from respective chemical containers. The system and method may involve two or more pairs of chemical and chemical container. Thus, the system and method may involve at least two pairs of chemical and chemical container. The system and method may involve a flow modulation sheet designed so as to control the flows of the chemicals. The flow modulation sheet may contain the target area. The system and method have the advantage of providing for accurate relative timing of the arrivals of the chemicals to the target area.

In some embodiments, the present disclosure pertains to a colorimetric system for detecting a substance, the colorimetric system that includes a first chemical container adapted for releasing a first chemical; a second chemical container adapted for releasing a second chemical; a flow modulation sheet adjacent each chemical container; and an encapsulation covering the flow modulation sheet and each chemical container, where the encapsulation comprises a window defining a target area of the filter paper such that the target area is adapted for applying the substance; where the flow modulation sheet comprises a design adapted for automatically controlling a first flow of the first chemical and a second flow of the second chemical to the target area after simultaneously releasing the first and second chemicals; and where the design comprises a first void disposed in the flow modulation sheet. In some embodiments the present disclosure pertains to a colorimetric method comprising providing the colorimetric system for detecting a substance; applying the substance to the target area; and simultaneously releasing the first and second chemicals.

Controlling the first and second flows may include controlling a first timing of the first flow and a second timing of the second flow. Controlling the first and second timings may include regulating a first speed of the first flow and a second speed of the second flow. Alternatively or in combination, controlling the first and second timings of the first and second flows comprises may include controlling a first arrival of the first chemical to the target area and a second arrival of the second chemical to the target area. The first arrival may be earlier than second arrival. The arrival a respective chemical may be the arrival of a leading edge of the flow of the respective chemical to an edge of the target area. The arrival of a respective chemical may be the arrival of at least 80% of the respective chemical to the full area of the target area. Controlling the first and second flows may include reducing dripping of the first and second chemicals. Reducing dripping of the first and second chemicals may include substantially preventing dripping of the first and second chemicals.

The colorimetric system and method may be adapted for upright use of the colorimetric system. The design of the flow modulation sheet may accommodate flows of the first and second chemicals under the influence of gravity.

The design of the flow modulation sheet may include a thickness of the void. The encapsulation may be made made by controlling bonding of a first encapsulation piece and a second encapsulation piece so as to control the thickness.

The design of the flow modulation sheet may include a shape of the first void. The shape may include a width and a length. The width may be less than the length. The size of the first void may be adapted to the viscosity of the first chemical, or a solution containing the first chemical in solution. For example, length may be increased with increasing viscosity.

The design of the flow modulation sheet may include a layout of the first void. The first void may be between the first chemical container and the target area. Further, the first void may be adjacent the first chemical container.

The design of the flow modulation sheet may include a second void disposed in the flow modulation sheet. The design of the flow modulation sheet may include a first shape of the first void and a second shape of the second void. The first shape may include a first length, the second shape may include a second length. The second length may be less than the first length. The difference in lengths may be adapted to delay the arrival of the second chemical to the target area relative to the arrival of the first chemical.

The design of the flow modulation sheet may include a layout of the first void and a layout of the second void. The second void may be between the second chemical container and the target area. A portion of the flow modulation sheet may be between the second void and the second chemical container. Alternatively, the second void may be adjacent the second chemical container.

The design of the flow modulation sheet may include a notch near the target area, where the notch is along a path of the second flow. The notch may be adapted for reducing dripping of the second chemical.

The flow modulation sheet may be made of a porous sheet of fibers. The porous sheet of fibers may be made of a porous paper. The first chemical containers may be made of a first ampoule. The first ampoule may be a glass ampoule. The second ampoule may be a second ampoule. The second ampoule may be a glass ampoule. The encapsulation may be made of plastic. The plastic may include polyvinyl chloride.

The first and second chemicals may be chemicals associated with the first stage and second stages respectively of a multiple stage colorimetric reaction scheme. The first chemical may be in a first solution. The second chemical may be in a second solution. It is within the skill of one of ordinary skill in the art to select a known multiple stage colorimetric reaction scheme. The first chemical may modify a molecular structure of the substance so as to produce an intermediate. The first chemical may break down the substance so as to produce an intermediate. The second chemical may be reactive with the intermediate so as to produce a color. The color may be detectable with the human eye. Alternative, or in combination, the color may be detectable with a detection device. For example, the color may be detectable with the spectral detection unit described in US20090325300.

The colorimetric system may be a colorimetric card. The colorimetric card may be suitable to use with the spectral detection unit. After inserting the colorimetric card into the spectral detection unit, the spectral detection unit may be used to initiate release of the chemicals. When the release is initiated manually, by pushing on a single portion of the spectral detection unit, the present colorimetric system and card and the advantage of that simultaneous release of the chemicals may be consistently repeated because both releases are initiated with the same push. Thus, the colorimetric system and method have the advantage of providing for accurate and consistent colorimetric testing.

DETAILED DESCRIPTION

Figure 1:
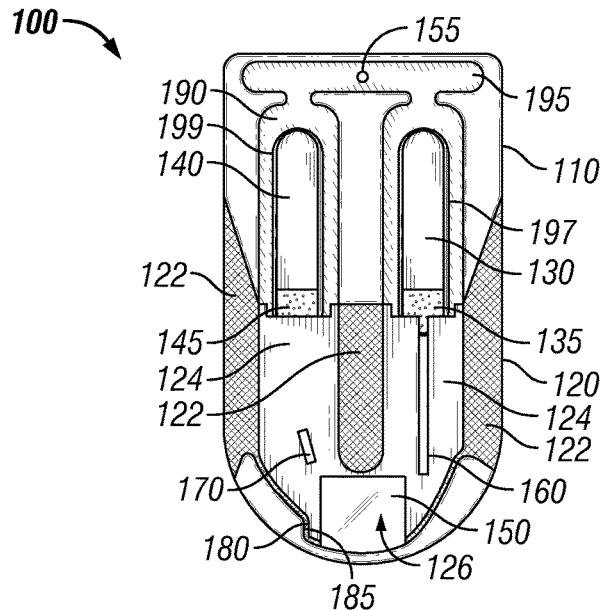
FIG. 1 shows a side view of an embodiment of the present colorimetric system.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Thus, for example, "includes" encompasses "includes, but is not limited to". Also, terms such as "element" or "component" encompass both elements or components comprising one unit and elements or components that comprise more than one unit unless specifically stated otherwise.

It is to be understood that "filter paper" is used herein to denote a porous nonwoven sheet of vegetable fibers. It is to be understood that as used herein "paper" denotes a felted, also termed nonwoven, sheet of fibers, where the fibers are vegetable fibers. Further, as used herein "filter paper" denotes porous paper. It is to be understood that the uses herein of "paper" and "filter paper" are consistent with the common meanings of "paper" and "filter paper". Exemplary vegetable fibers known to one of ordinary skill in the art are wood fibers, cotton fibers, and the like. It is within the skill of ordinary skill in the art to select a suitable nonwoven porous sheet of vegetable fibers. For example, wood-based filter paper and cotton-based nonwoven buckram paper are each a suitable porous paper for the present system and method.

It is to be understood that "channel" as used herein denotes a region suitable for flow. It is to understood that as used herein "air channel" denotes a channel provided as a void. It is to be understood that, when in use, an air channel may receive a flow of a chemical there through.

The elements used in the present disclosure provide timing control and sequencing of different chemicals with much greater accuracy. The present disclosure, details how expanded and enhanced tests can be performed, which significantly expand the test capabilities of the colorimetric approach and how they can be used in real world applications. Controlling the flow of chemical in automated colorimetric systems tends to involve controlled release of the chemical (gating), as well as control of the chemical as to when it reaches the target area for the colorimetric reaction post gating. Gating of the chemical is the primary determining factor that establishes the gross timing. However, precise control of the timing for the chemical to reach the targeted area, can provide enhanced colorimetric testing that could not be achieved with other methods. Precise control of the chemical flow after gating can be achieved by utilizing various methods to control the overall timing. This is especially desirable when timed sequential gating is not an option.

In some embodiments, the present disclosure pertains to mechanisms to sequence and control the flow of chemicals in defined environments. In some embodiments, the chemical is stored in a chemical container. In some embodiments, a glass ampoule would be an example of a chemical container. Thereafter, the chemical can be released from the chemical container in a controlled fashion. In some embodiments, a timing component may be present, where chemicals can be released together. It will be understood that "released together" denotes released simultaneously.

The present approach allows for the sequencing of chemicals so that certain substances can be detected that require multiple reactions to be detected. Sequencing is the process of controlling the arrival of a chemical to a targeted "test area" in an automated fashion so that multiple individual chemical reactions can take place. This is desirable in some colorimetric tests where a prior chemical reaction modifies the characteristics of the substance under test in order to be able to execute a subsequent test that requires molecular modification prior to testing for a particular substance.

In various embodiments, chemical flow from a chemical container to a test area can be controlled by implementation of a filter paper mechanism, with suitable material characteristics, coupled with design structures of the paper layout that influence chemical flow. The filter paper modulates flow characteristics of chemicals therein. Therefore filter paper is illustrative herein of a flow modulation sheet.

Design structures of the filter paper include design of an air channel, which has a first order effect on the chemical flow. Thickness of the card and compression of the filter paper can also be uniquely specified to control chemical flow. In some embodiments, this can be accomplished by control of the bonding mechanism used to encapsulate the filter paper.

In various embodiments, the elements used in the present disclosure include, without limitation, implementing an "air" channel in a filter paper, tighter control of the RF welding process in order to control thickness of the air channel, and modifying the shape characteristics of the channel to modify chemical flow behavior. Examples of these variations are illustrated in FIGS. 1-9 and described herein.

Referring now to FIG. 1, colorimetric system 100 includes encapsulation 110, filter paper 120, first chemical container 130, second chemical container 140, window 150, first air channel 160, second air channel 170, notch 180, and main channel 190. First chemical 135 is contained in first container 130. Second chemical 145 is contained in second container 140. Main channel 190 is U-shaped and has two subchannels, one for each combination of chemical container and air channel. Filter paper 120 includes discontinuous portions 122 outside of alignment with main channel 190 and continuous portion 124 aligned with main channel 190. Notch 180 is in filter paper 120. Notchmate 185 is in encapsulation 110. Notchmate 185 aligns with notch 180. Filter paper 120 includes first air channel 160 therethrough and second air channel 170 therethrough. Filter paper 120 includes test area 126. Test area 126 is defined by window 150. Encapsulate 110 includes window 150 therethrough. Encapsulate 110 includes first cavity 197 therein and second cavity 199 therein. First container 130 rests in first cavity 197. Second container 140 rests in second cavity 199. Air vent channel 195 is connected to main channel 190. Encapsulation 110 includes hole 155 therethrough. Hole 155 is aligned so as to provide an opening to air vent channel 195.

Figure 2:
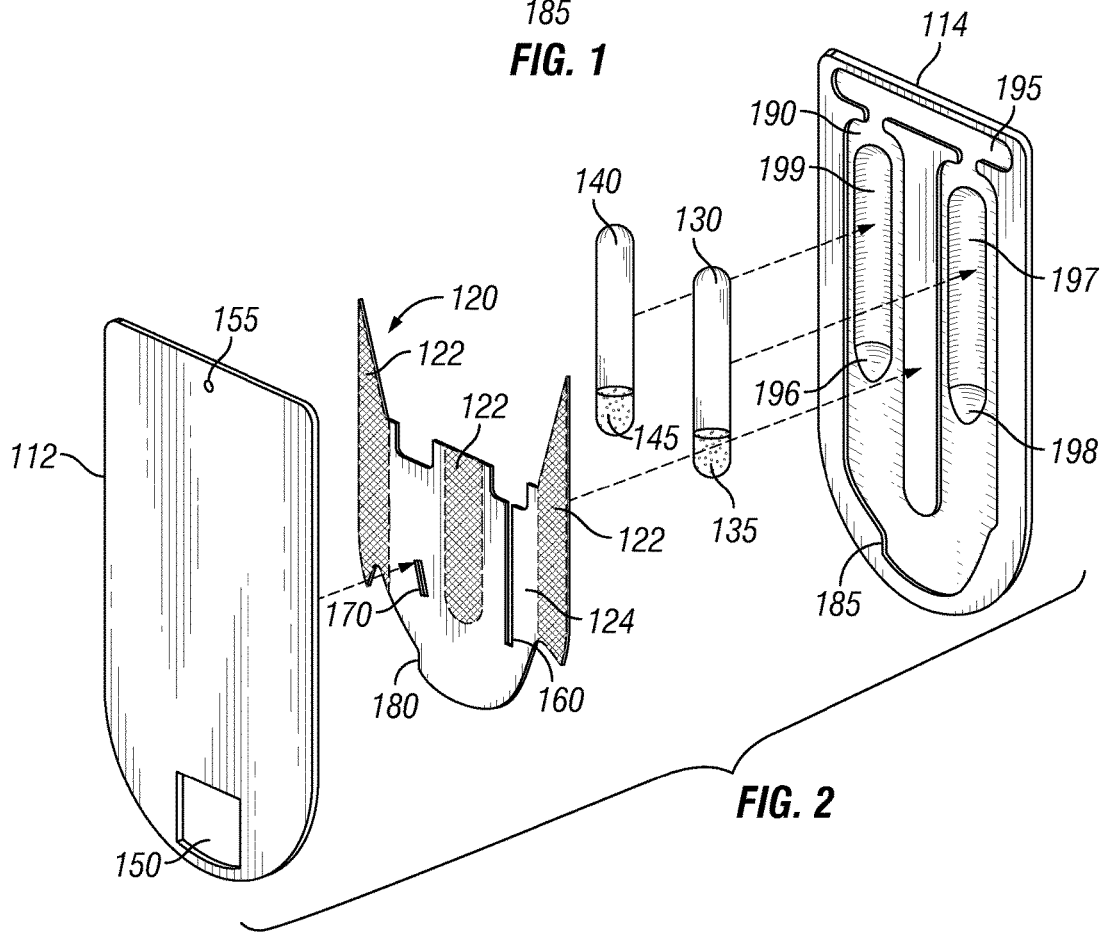
FIG. 2 shows an exploded view of the embodiment shown in FIG. 1.
Figure 3:
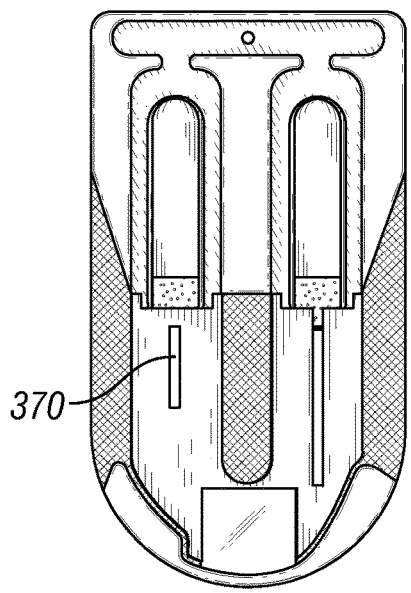
FIG. 3 shows a side view of an alternative embodiment of the present colorimetric system.
Figure 4:
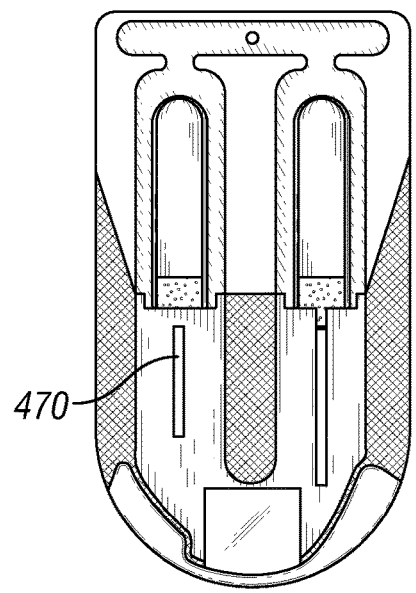
FIG. 4 shows a side view of another alternative embodiment of the present colorimetric system.
Figure 5:
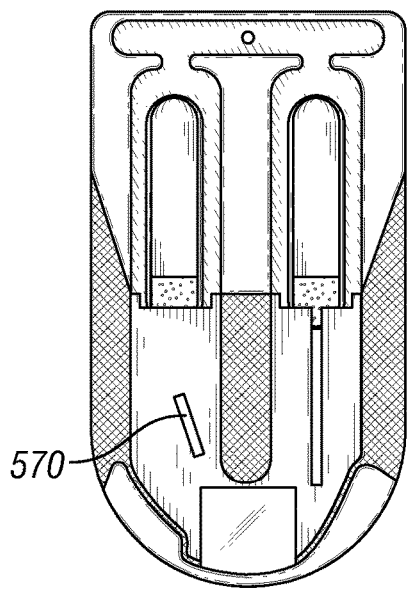
FIG. 5 shows a side view of yet another alternative embodiment of the present colorimetric system.
Figure 6:
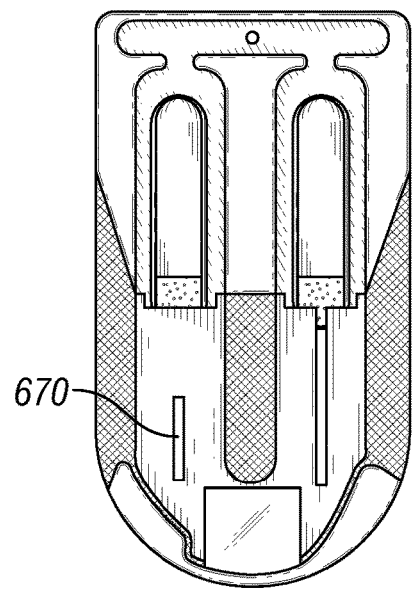
FIG. 6 shows a side view of still another alternative embodiment of the present colorimetric system.

Referring now to FIG. 2, an exploded view of colorimetric system 100 is shown. First encapsulate piece 114 and second encapsulate piece 112 are bonded to form encapsulate 110.

In some embodiments, physical characteristics of the air channel can be used to regulate the speed of fluid flow in the test card. In some embodiments, the length, width and shape of the air channel can be adjusted to influence the fluids dynamics of the flow.

Referring now to FIGS. 3-6, various alternative second air channels 370, 470, 570, and 670 are shown. The variations illustrate variations in layout and length of an air channel.

Figure 7:
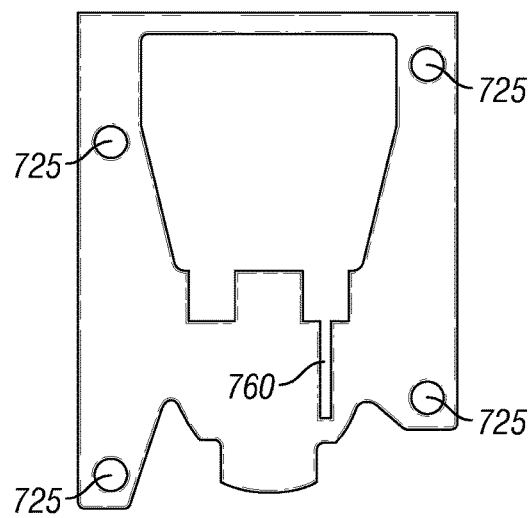
FIG. 7 shows a side view of an embodiment of a filter paper before assembly and trimming.
Figure 8:
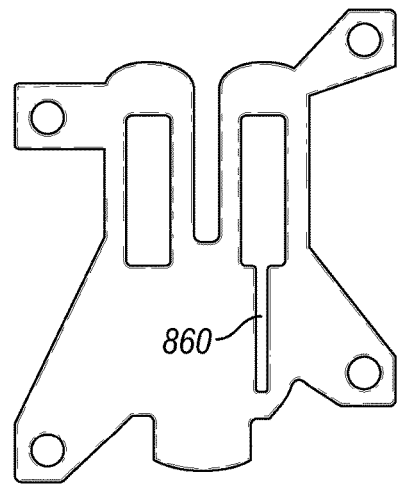
FIG. 8 shows a side view of an alternative embodiment of a filter paper before assembly and trimming.
Figure 9:
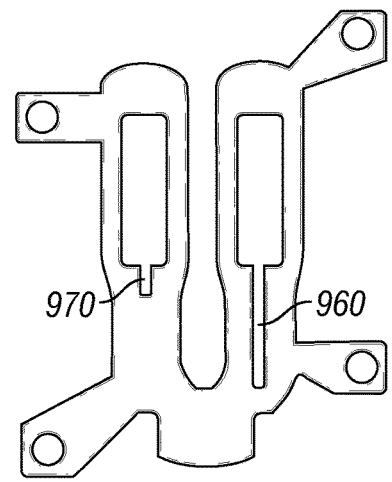
FIG. 9 shows a side view of another alternative embodiment of a filter paper before assembly and trimming.

Referring now to FIG. 7 first air channel 760 and registration holes 725 are shown in a filter paper before assembly and trimming. Referring to FIGS. 8-9, various alternative first air channels 860, and 960 are shown and an alternative second air channel 970 is shown.

Welding specifications of the plastic encapsulation also affects chemical flow and is controlled based upon the materials and filter paper design used. Design considerations for the card are reflected in the method of making the card. The welding, also termed bonding herein, involves use of aluminum tools for radiofrequency (RF) heating of the plastic encapsulation. Some design considerations follow.

Installing an air vent channel may include modifying a thermoform mold tool to put an indentation in the air vent channel. Installing an air vent channel may further include, during cut and trim operation, inserting a hole using the indentation as a locator. This maintains the consistency of the location and size of the air vent hole. The air vent hole may be punched in the encapsulation after welding.

Making the card edges smooth may include making a top RF tool and a bottom RF tool oversized. Making the card edges smooth may further include cutting the card from the resulting oversized welded parts. This moves the edge of the RF weld out. Therefore when cut in the cutting tool, the edge will be smooth. Before welding, oversize components having registration holes may be aligned using the registration holes. Referring to FIG. 7, registration holes 725 are illustrated. Both filter paper and first and second encapsulation pieces may be oversized before aligning, welding, and cutting.

Modifying the main channel so liquid enters at more contact points to the path may include adjusting the width of the main channel. Adjusting the width of the main channel may include adjusting the RF insulator. Adjusting the width of the main channel may include adjusting a thermoform mold. Adjusting the thermoform mold permits adding channels to direct flow to saturate the pad, also termed herein the test area, also termed herein the target area, from the back side as well as the edges.

A Rayform channel support may be used. It is desirable to mill the Rayform insert to fit exactly with the main channel part of the mold.

It will be understood that the above description reveals that the present colorimetric system may be made by providing a bottom RF mold, an RF insulation, and a Rayform insert; placing a back encapsulation precursor having registration holes over the bottom RF mold, inserting first and second chemical containers; inserting a filter paper precursor having registration holes; adding a front encapsulation precursor having registration holes; topping with a top RF mold; aligning the precursors; applying RF heat so as to bond the back and front encapsulation pieces; and trimming the precursors.

Embodiments of the present disclosure can be used to detect substances that require more than one chemical reaction to perform a colorimetric reaction. Embodiments include having to use a chemical reaction to modify the molecular structure of a substance before a second defined chemical reaction can be executed to provide for the colorimetric reaction process to identify the substance in the colorimetric reaction. An example of this embodiment is if a particular molecule needs to be cleaved off by a prior reaction, before the colorimetric test will work. By controlling the chemical flow and having chemical #1 react, prior to having chemical #2 being introduced to the subject test area, sequential chemical reactions can be produced in a control fashion that otherwise would not be possible. In various embodiments, timing of chemical flow is an important component to repeatable and reliable reactions.

By way of example and not limitation, the present colorimetric system and device are suitable for controlling the conventional two stage colorimetric Griess-based reaction scheme to test for nitroglycerin.

The methods and apparatus of the present disclosure have significant flexibility in design and implementation. Therefore, the methods and apparatus of the present disclosure are adaptable to many different types of conditions.

Furthermore, in various embodiments, additional types of chemicals can be added to provide more complex molecule manipulation and therefore detection, which cannot be achieved with other means.

In some embodiments, chemical flow characteristics can be adjusted and modified based on manipulating chemical viscosity through adjustment of water to solvent ratios. There are many ways by which to use the chemical viscosities to adjust flow. More than two chemicals can be added to the card, which would involve further chemical flow parameters.

Furthermore, chemical flow may sometimes be impeded by a high concentration of acid used in the detection chemical makeup. Therefore, in various embodiments, different techniques of stimulating the flow of acids can be employed by changing channel design and layout. In various embodiments, ventilation and doping materials may also be used to affect chemical flow. Additional methods may also be used to adjust the filter paper and channel makeup in the chemical flow process that can be vetted and utilized.

Further refinement and control of the chemical flow can also be possible. Such refinements can lead to increased repeatability in the testing, as well faster test results. This can provide additional advantages of the historical method of manually sequencing this type of test as the total test time can be reduced, which can dramatically improve utilization of this process in the marketplace.

The implementation of automated control of this chemical sequencing eliminates manual intervention and provides much higher reliability and quality of control where sequential chemical reactions are required.

An advantage of utilizing the methods and apparatus of the present disclosure is that they greatly expand the capabilities of a colorimetric test. With control of chemical flow as described, Applicants can make a device that can test many substances that previously could not be tested in a controlled and/or automated fashion. By controlling the flow of chemicals in a quantitative, repeatable fashion, dramatically improved repeatability and quality of the chemical process is achievable.

Without further elaboration, it is believed that one skilled in the art can, using the description herein, utilize the present disclosure to its fullest extent. The section headings used herein are for organizational purposes and are not to be construed as limiting the subject matter described. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A system for detecting a substance, the system comprising:
   a first chemical container adapted for releasing a first chemical;
   a second chemical container adapted for releasing a second chemical;

a flow modulation sheet comprising a target area adapted for applying the substance;
   wherein the flow modulation sheet further comprises a porous sheet adapted for automatically controlling a first flow of the first chemical and a second flow of the second chemical to the target area after simultaneously releasing the first and second chemicals,
   wherein the porous sheet comprises a first portion near the first chemical container, and a second portion near the second chemical container,
      wherein the first portion of the porous sheet comprises a first air channel disposed between the first chemical container and the target area,
      wherein the second portion of the porous sheet comprises a second air channel disposed between the second chemical container and the target area, and
      wherein the first air channel and the second air channel have different chemical flow characteristics.

2. The system for detecting a substance according to claim 1, further comprising an encapsulation covering the flow modulation sheet and each chemical container, wherein the encapsulation comprises a window defining the target area.

3. The system for detecting a substance according to claim 2, wherein the encapsulation comprises a plastic.

4. The system for detecting a substance according to claim 3, wherein the plastic comprises polyvinyl chloride.

5. The system for detecting a substance according to claim 1, wherein the first air channel and the second air channel have different lengths, and wherein the different lengths contribute to the different chemical flow characteristics.

6. The system for detecting a substance according to claim 1, wherein the porous sheet comprises a porous sheet of fibers.

7. The system for detecting a substance according to claim 6, wherein the porous sheet of fibers comprises a porous paper.

8. The system for detecting a substance according to claim 1, wherein first and second chemical containers comprise first and second glass ampoules, respectively.

9. The system for detecting a substance according to claim 1, wherein the different chemical flow characteristics comprise different speeds of fluid flow.

10. The system for detecting a substance according to claim 1, wherein the first air channel comprises a void within the first portion of the porous sheet.

11. The system for detecting a substance according to claim 1, wherein the second air channel comprises a void within the second portion of the porous sheet.

12. A method for detecting a substance, comprising:
applying the substance to a target area of a system, wherein the system comprises:
   a first chemical container adapted for releasing a first chemical;
   a second chemical container adapted for releasing a second chemical;
   a flow modulation sheet comprising the target area;
      wherein the flow modulation sheet further comprises a porous sheet adapted for automatically controlling a first flow of the first chemical and a second flow of the second chemical to the target area,
      wherein the porous sheet comprises a first portion near the first chemical container, and a second portion near the second chemical container,
      wherein the first portion of the porous sheet comprises a first air channel disposed between the first chemical container and the target area,
      wherein the second portion of the porous sheet comprises a second air channel disposed in the flow modulation sheet between the second chemical container and the target area, and
      wherein the first air channel and the second air channel have different chemical flow characteristics; and
simultaneously releasing the first and second chemicals.

13. The method of claim 12, wherein controlling the first and second flows comprises controlling a first timing of the first flow and a second timing of the second flow by regulating a first speed of the first flow and a second speed of the second flow.

14. The method of claim 12, wherein controlling the first and second flows comprises controlling a first timing of the first flow and a second timing of the second flow by controlling a first arrival of the first chemical to the target area and a second arrival of the second chemical to the target area.

15. The method of claim 14, wherein the first flow of the first chemical arrives at the target area earlier than the second flow of the second chemical.

* * * * *